United States Patent [19]

Meilland

[11] Plant 4,625

[45] Jan. 20, 1981

[54] ROSE PLANT-MEIGRONURI VARIETY

[75] Inventor: Marie-Louise Meilland, Antibes, France

[73] Assignee: The Conard-Pyle Company, West Grove, Pa.

[21] Appl. No.: 51,237

[22] Filed: Jun. 22, 1979

[51] Int. Cl.[3] ..... A01H 5/00

[52] U.S. Cl. ..... Plt./24

[58] Field of Search ..... Plt./24

*Primary Examiner*—Robert E. Bagwill

*Attorney, Agent, or Firm*—Burns, Doane, Swecker & Mathis

[57] ABSTRACT

A rose plant of the Floribunda class is provided having abundant long lasting double flowers which are lemon yellow suffused with buttercup yellow. The seed parent of the new variety was the variety Poppy Flash and the pollen parent resulted from the crossing of the variety Meiridge with the variety Allgold. The vegetation of the new variety is vigorous.

14 Drawing Figures

SUMMARY OF THE INVENTION

The object of the present invention is to provide a new variety of rose plant of the Floribunda class which is distinguished from prior varieties by the following characteristics:

(1) from the physical point of view the plant is bushy, the mature wood is light green, the flower is double, and the petals are of a lemon yellow color suffused with buttercup yellow; and (2) from the biological point of view the vegetation is vigorous, the flowering habit is very abundant, the flowers are long lasting, and the petals drop off cleanly.

In view of these characteristics the new variety meets the needs of the horticultural industry for all purposes, and particularly is suited for the ornamentation of gardens and parks.

The new variety was created by artificial pollination whereby two genitors were combined which previously had been studied for the possession of the characteristics sought in the new variety.

The seed parent of the new variety was the variety Poppy Flash (non-patented). The pollen parent of the new variety resulted from the crossing of the variety Meiridge (non-patented) and the variety Allgold (U.S. Plant Pat. No. 1,665).

This parentage of the new variety may be expressed as follows:

POPPY FLASH × (MEIRIDGE × ALLGOLD)

The seeds resulting from the above pollination were sown and 806 plantlets were obtained which were physically and biologically different from each other. Selective study resulted in the identification of a single plant of the new variety. This plant was very vigorous and produced flowers of the above-identified coloration persistently and abundantly to yield a large mass effect. Extensive testing has confirmed the behavior and characteristics of the new variety which is particularly suited for growing in the open air in gardens and parks.

The characteristics and properties of the new variety have been found to be transmissible by agamic means, also called "asexual", i.e. by means of vegetative propagation, in particular by grafting an eye. The rose plant of the new variety has been designated the Meigronuri variety.

BRIEF DESCRIPTION OF THE PHOTOGRAPH

The accompanying photograph shows as nearly true as it is reasonably possible to make the same in a color illustration of this character typical specimens of cut flowers and foliage of the new variety grown in the open air at Cannet des Maures, France, illustrated in:

FIG. 1 — a specimen of the young shoot;

FIG. 2 — a specimen of several buds wherein the sepals of the center bud are beginning to open;

FIG. 3 — a specimen of the bud at the opening of the petals;

FIG. 4 — a specimen of the flower in the course of opening;

FIG. 5 — a specimen of the fully open flower seen from the obverse;

FIG. 6 — a specimen of the fully open flower seen from the reverse;

FIG. 7 — a specimen of the receptacle showing the arrangement of the stamens;

FIG. 8 — a specimen of the receptacle showing the arrangement of the pistils (sepals and stamens removed);

FIG. 9 — a specimen of the fruit;

FIG. 10 — a portion of a main stem;

FIG. 11 — a portion of a flowering stem;

FIG. 12 — a specimen of a leaf with 5 leaflets, upper surface;

FIG. 13 — a specimen of a leaf with 7 leaflets, under surface; and

FIG. 14 — a specimen of a leaf with 3 leaflets, upper surface.

DETAILED DESCRIPTION

Figures 1, 2, 3, 4, 5, 6, 7, 8, 9, 10, 11, 12, 13, 14:
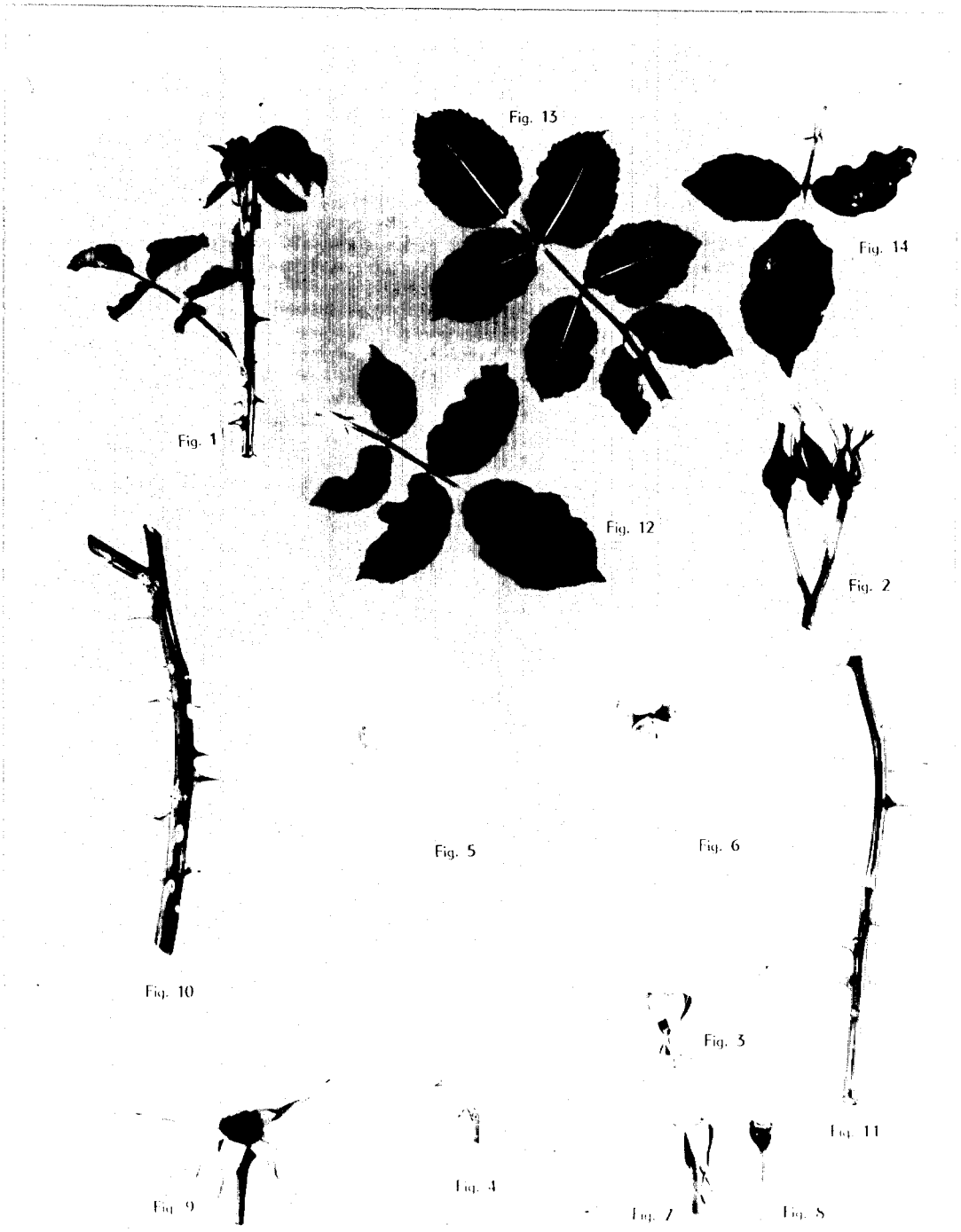

The plant described was grown in the open air at Cannet des Maures, France.

The chart utilized in the identification of the colors is that of the Royal Horticultural Society (R.H.S. Colour Chart). The terminology preceding the numbered references to this chart has been added to designate in common terms the corresponding colors.

Class: Floribunda.

Plant:

*Height.*—Approximately 0.7 meters on the average.

*Habit.*—Bushy.

Branches:

*Color.*—Young stems: bronzed green 146/A (yellow green group). Mature wood: light green 146/B (yellow green group).

*Prickles.*—Shape: straight upper edge, concave lower edge. Size: average to small. Quantity: average to small. Color: young stems: reddish. Color: mature wood: greenish pink then havanna brown.

Leaves:

*Stipules.*—Adnate, pectinate, rather narrow and linear.

*Petioles.*—Obverse: ribbed, light slightly reddish green on young foliage, average green on mature foliage, edges more or less glandular. Reverse: light green, bearing some small curved prickles.

*Leaflets.*—Number: 3 or 5 (most often), and 7 (frequently). Shape: oval, with lanceolate tip. Teeth: simple and regular. Texture: leathery. General effect: averagely abundant foliage, thick and half dull in appearance. Color: young foliage. Obverse: bronzed green 146/A (yellow green group), more or less speckled with reddish coloration. Reverse: average green 147/B (yellow green group), more or less speckled with reddish coloration. Color: mature foliage. Obverse: dark green 147/A (yellow green group). Reverse: average green 147/B (yellow green group).

Inflorescence:

*Number of flowers.*—Generally pluriflore (e.g. from 1 to 10 flowers per stem).

*Peduncle.*—Straight, rigid, slightly tomentose, more or less speckled with reddish coloration, approximately 3.2 cm. long.

*Sepals.*—Obverse: tomentose, greenish, more or less speckled with reddish coloration. Reverse: light green, more or less speckled with reddish coloration. The edges of the external sepals are glandular and slightly appendiculate.

*Bud.*—Shape: conical. Length: on an average approximately 2.3 cm. out of calyx, at the opening of the sepals. Size: medium. Color: when opening. Obverse: lemon yellow 14/A (yellow green group) suffused with buttercup yellow 15/A (yellow green group) on the edge. Reverse: lemon yellow 14/A (yellow green group) suffused with buttercup yellow 15/A (yellow green group) on the edge.

*Flower.*—Shape: full initially, then opens as a cup with the stamen showing. Duplicature: double. Diameter: on an average approximately 8 cm. Color: when opening. Obverse: lemon yellow 14/A (yellow green group) suffused with buttercup yellow 15/A (yellow green group) on the edge. Reverse: lemon yellow 14/A (yellow green group) suffused with buttercup yellow 14/B (yellow green group) on the edge. Color: during the course of opening. Obverse: lemon yellow 14/B (yellow green group) suffused with buttercup yellow 15/B (yellow green group) on the edge. Reverse: lemon yellow 14/B (yellow green group) suffused with chromium yellow 15/C (yellow green group) on the edge. Color: when fully open. Obverse: lemon yellow 14/B (yellow green group) suffused with chromium yellow 15/D (yellow green group) on the edge, then barium yellow 10/C (yellow group) more or less speckled with carmine. Reverse: lemon yellow 14/C (yellow green group) largely suffused with chromium yellow 15/D (yellow green group) on the edge, then barium yellow 10/D (yellow group) more or less speckled with carmine. Fragrance: none. Lasting quality: long. Corolla: petals. Texture: consistent. Shape: top well rounded and sometimes indented, cuneiform base. Number: approximately 35 to 40 commonly with one false petal and several petals not quite full in the center. Shedding petals: the petals drop off cleanly. Stamens: number: on an average approximately 65. Anthers: normal, yellow. Filaments: yellow. Pistils: number: on an average approximately 75. Stigmas: normal, yellowish. Styles: yellowish, slightly twisted and tomentose. Receptacle: light green, more or less spotted with reddish brown coloration (common terms) at the dehiscence of the anthers, and in longitudinal section it is narrow and vase shaped.

Development:

*Vegetation.*—Vigorous.

*Blossoming.*—Very abundant.

*Aptitude for setting fruit.*—Medium.

*Resistance to frost.*—Spring: good. Winter: good.

*Resistance to diseases.*—Not especially susceptible to cryptogramic diseases.

I claim:

1. A new and distinct variety of Floribunda rose plant characterized by the fact that:

from the physical point of view the plant is bushy, the mature wood is light green, the flower is double and the petals are of a lemon yellow color suffused with buttercup yellow; and from the biological point of view the vegetation is vigorous, the flowering habit is very abundant, the flowers are long lasting, and the petals drop off cleanly;

substantially as shown and described.

* * * * *